United States Patent
Massari et al.

(10) Patent No.: US 12,329,736 B2
(45) Date of Patent: Jun. 17, 2025

(54) CARBOXYLATE LIGAND MODIFIED FERRIC IRON HYDROXIDE COMPOSITIONS FOR USE IN THE TREATMENT OR PREVENTION OF IRON DEFICIENCY ASSOCIATED WITH LIVER DISEASES

(71) Applicant: Nemysis Ltd., Dublin (IE)

(72) Inventors: Danilo Casadei Massari, London (GB); Maria Cristina Comelli, Padua (IT); Jonathan Powell, Cambridge (GB); Nuno Faria, Milton Ernest (GB); Katharina Kessler, Oxford (GB)

(73) Assignee: Nemysis Ltd., Dublin (IE)

( * ) Notice: Subject to any disclaimer, the term of this patent is extended or adjusted under 35 U.S.C. 154(b) by 321 days.

(21) Appl. No.: 17/915,192

(22) PCT Filed: Apr. 1, 2021

(86) PCT No.: PCT/EP2021/058743
§ 371 (c)(1),
(2) Date: Sep. 28, 2022

(87) PCT Pub. No.: WO2021/204705
PCT Pub. Date: Oct. 14, 2021

(65) Prior Publication Data
US 2023/0134391 A1    May 4, 2023

(30) Foreign Application Priority Data
Apr. 6, 2020  (GB) .................................. 2005054

(51) Int. Cl.
*A61K 31/295* (2006.01)
*A61K 33/26* (2006.01)
*A61P 1/16* (2006.01)
*A61P 7/06* (2006.01)

(52) U.S. Cl.
CPC .............. *A61K 31/295* (2013.01); *A61P 1/16* (2018.01); *A61P 7/06* (2018.01); *A61K 33/26* (2013.01)

(58) Field of Classification Search
CPC ......... A61K 31/295; A61K 33/26; A61P 1/16; A61P 7/06
See application file for complete search history.

(56) References Cited

U.S. PATENT DOCUMENTS

| | | |
|---|---|---|
| 3,076,798 A | 2/1963 | Arthur et al. |
| 3,821,192 A | 6/1974 | Montgomery et al. |
| 2006/0205691 A1 | 9/2006 | Geisser et al. |
| 2013/0109730 A1 | 5/2013 | Alberti et al. |

FOREIGN PATENT DOCUMENTS

| | | |
|---|---|---|
| JP | 2013082726 A | 5/2013 |
| WO | 2003092674 A1 | 11/2003 |
| WO | 2003097627 A1 | 11/2003 |
| WO | 2006037449 A2 | 4/2006 |
| WO | 2008096130 A1 | 8/2008 |
| WO | 2012144619 A1 | 10/2012 |
| WO | 2016170152 A1 | 10/2016 |
| WO | 2016206699 A1 | 12/2016 |
| WO | 2017060441 A1 | 4/2017 |

OTHER PUBLICATIONS

Aslam et al., "Ferroportin mediates the intestinal absorption of iron from a nanoparticulate ferritin core mimetic in mice," FASEB Journal 28(8):3671-3678 (2014).
Bobtelsky et al., "The structure and behaviour of ferric tartrate and citrate complexes in dilute solutions," J.A.C.S., 69:2286-2290 (1947).
Geisser et al., "Pharmacokinetics of iron salts and ferric hydroxide-carbohydrate complexes," Arzneimittelforshung/Drug Research 37(1):100-104 (1987).
Harvey et al., "Ferric trimaltol corrects iron deficiency anaemia in patients intolerant to iron," Alimentary Pharmacology & Therapeutics 12(9):845-848 (1998).
Heinrich, "Bioavailability of trivalent iron in oral preparations," Arzeinmittelforshung/Drug Research 25(3):420-426 (1975).
Broadwith, "Solving iron's solubility problem," Chemistry World, downloaded from https://www.chemistryworld.com/news/solving-irons-solubility-problem/8066.article, 4 pages (2014).
Nielsen et al., "Bioavailability of iron from oral ferric polymaltose in humans," Arzneimittelforshung/Drug Research 44(1):743-748 (1994).
Powell et al., "A nano-disperse ferritin-core mimetic that efficiently corrects anaemia without luminal iron redox activity," Nanomedicine 10(7):1529-1538 (2014).
International Search Report and Written Opinion issued in PCT/EP2021/058743, mailed Jul. 7, 2021, 12 pages.
Pereira et al., "A novel nano-iron supplement to safely combat iron deficiency an anaemia in young children: The HAT-GUT double-blind, randomised, placebo-controlled trial protocol", Gates Open Research 2(48):1-22 (2019).
Pereira et al., "Nanoparticle iron(III) oxo-hydroxide delivers safe iron that is well absorbed and utilised in humans", Nanomedicine: NBM 10:1877-1886 (2014).
Search Report issued in GB 2005054.8, dated Sep. 22, 2022, 2 pages.

*Primary Examiner* — Theodore R. Howell
(74) *Attorney, Agent, or Firm* — McNeill PLLC

(57) ABSTRACT

The use of carboxylate ligand modified ferric iron hydroxide compositions for the treatment or prevention of iron deficiency associated with liver diseases is disclosed, and more particularly to the class of Iron Hydroxide Adipate Tartrate (IHAT) materials for 10 use in the treatment or prevention of iron deficiency associated with non-alcoholic fatty liver disease (NAFLD) or non-alcoholic steatohepatitis (NASH).

23 Claims, 1 Drawing Sheet

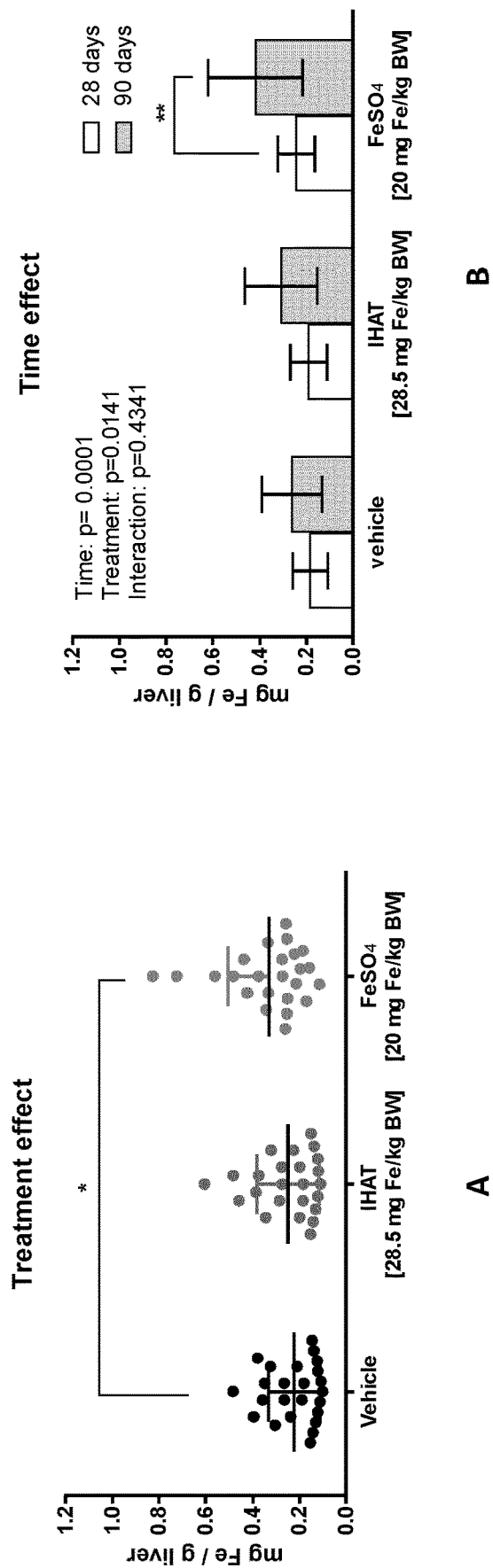

CARBOXYLATE LIGAND MODIFIED FERRIC IRON HYDROXIDE COMPOSITIONS FOR USE IN THE TREATMENT OR PREVENTION OF IRON DEFICIENCY ASSOCIATED WITH LIVER DISEASES

CROSS-REFERENCE TO RELATED APPLICATIONS

This application is a national phase entry pursuant to 35 U.S.C. § 371 of International Application No. PCT/EP2021/058743, filed Apr. 1, 2021, which claims the benefit of priority of United Kingdom (GB) patent application number 2005054.8 filed Apr. 6, 2020, each of which is incorporated herein by reference in its entirety for any purpose.

FIELD OF THE INVENTION

The present invention relates to carboxylate ligand modified ferric iron hydroxide compositions for use in the treatment or prevention of iron deficiency associated with liver diseases, and more particularly to the class of Iron Hydroxide Adipate Tartrate (IHAT) materials for use in the treatment or prevention of iron deficiency associated with non-alcoholic fatty liver disease (NAFLD) or non-alcoholic steatohepatitis (NASH) in a subject.

BACKGROUND OF THE INVENTION

Despite considerable global efforts with oral iron supplementation and fortification, iron deficiency remains the most common and widespread nutritional disorder in the world. A key reason for this failure is that, to address iron deficiency, oral iron supplementation needs to be well tolerated, cheap, safe and effective. However, currently available preparations fail in at least one of these criteria. Simple ferrous iron [Fe(II)] salts are most commonly used as these are inexpensive and the iron is well absorbed. However, these are poorly tolerated and indeed appear to enhance systemic infection rates, may induce undesirable changes to commensal bacteria of the colon and increase pro-inflammatory signalling of the gut epithelium. Some forms of ferric iron [Fe(III)] are considered safer and better tolerated in the gut lumen than Fe(II), but have the disadvantage that they are poorly absorbed and/or expensive. Accordingly, there is a general problem in the art that forms of iron supplements often have undesirable side effects or properties that make them difficult to use in certain clinical situations.

WO 2008/096130 (Medical Research Council) describes ferric iron oxo-hydroxide colloids that are modified synthetically so that dietary carboxylic acid ligands are non-stoichiometrically incorporated into the iron oxo-hydroxide structure. These colloidal ligand modified iron oxo-hydroxides, in which the mineral phase is disrupted, mimic the ferritin core—a natural dietary source of iron—and thus are well absorbed in humans with few or no side effects, providing a safe and efficacious oral iron supplement. The ligand modified ferric oxo-hydroxides described in WO 2008/096130 include nanoparticles of iron hydroxide modified with adipate (A) and tartrate (T) carboxylate ligands, a class of materials referred to as Iron Hydroxide Adipate Tartrate or "IHAT", see http://www.rsc.org/chemistryworld/2014/12/solving-iron-solubility-problem-profile-mrc).
Unlike many of the iron absorption materials referred to above these materials are shown to be safe iron delivery agents and their absorption in humans correlated with serum iron increase (P<0.0001) and direct in vitro cellular uptake (P=0.001), but not with gastric solubility. IHAT also showed ~80% relative bioavailability to Fe(II) sulfate in humans and, in a rodent model, IHAT was equivalent to Fe(II) sulfate at repleting haemoglobin. Furthermore, unlike Fe(II) sulfate, IHAT promoted a beneficial microbiota. In cellular models, IHAT was 14-fold less toxic than Fe(II) sulfate/ascorbate, itself has minimal acute intestinal toxicity in cellular and murine models and shows efficacy at treating iron deficiency anaemia (Pereira et al., Nanoparticulate iron(III) oxo-hydroxide delivers safe iron that is well absorbed and utilised in humans, Nanomedicine, 10(8): 1877-1886, 2014). Other papers describing IHAT and its uses for treating iron deficiency include Aslam, et al., Ferroportin mediates the intestinal absorption of iron from a nanoparticulate ferritin core mimetic in mice (FASEB J. 28(8):3671-8, 2014) and Powell et al., A nano-disperse ferritin-core mimetic that efficiently corrects anaemia without luminal iron redox activity (Nanomedicine. 10(7):1529-38, 2014).

IHAT materials are produced in WO 2008/096130 by co-precipitating ferric iron ions and the organic acids by raising the pH of an aqueous solution of the components from a pH at which they are soluble to a higher pH at which polymeric ligand modified ferric oxo-hydroxide forms. The precipitate is then dried, either by oven drying at 45° C. for 4-14 days or freeze-drying at −20° C. and 0.4 mbar for a longer period, thereby producing ligand modified ferric oxo-hydroxide suitable for formulation as an iron supplement.

In WO 2017/060411, the inventors described an improved synthesis and purification of carboxylate modified ferric oxo-hydroxides such as IHAT. In this synthesis, ligand modified ferric iron oxo-hydroxide was produced by reacting ferric chloride with sodium hydroxide in the presence of carboxylate ligands, such as tartaric acid and adipic acid. The resulting product was a suspension of colloids that are very small (i.e., small nanoparticles) and not amenable to purification using centrifugation. The synthesis therefore used a non-aqueous solvent, such as ethanol, to induce the aggregation of the ligand modified ferric iron hydroxide colloids and the resulting aggregated material was then recovered through filtration or centrifugation. This synthesis improved over the one described in WO 2008/096130 as it reduced the degree of particle agglomeration that leads to material that may not re-disperse once back in water and avoids products in which unreacted starting materials are present. Thus, the synthesis disclosed in WO 2017/060411 produced IHAT compositions with a microparticulate ferric iron fraction comprising less than 3.0% of the total ferric iron present in the material when dispersed in water at a concentration of 40 mM Fe.

SUMMARY OF THE INVENTION

Non-alcoholic fatty liver disease (NAFLD) is a condition in which excess fat is stored in the liver that is not caused by heavy alcohol use without inflammation or liver damage. NAFLD can progress to non-alcoholic steatohepatitis (NASH), cirrhosis and eventually hepatocellular carcinoma. NASH is diagnosed from histopathological examination of a liver biopsy where this shows fat along with inflammation and damage to liver cells. NASH affects 3-4% in the United States population whilst NAFLD is becoming the most common liver disease worldwide with an estimated prevalence of 25%-30%.

Importantly, while one third of adult patients with NAFLD are considered to be iron deficient, there is evidence that iron is a co-factor in the pathogenesis of NASH. This means that it would be considered undesirable to have hepatic loading of iron in NAFLD (as a risk factor that could convert it to NASH), or in NASH itself (as a co-morbidity issue). As a patient group, subjects with NALFD or NASH represent about a quarter of all iron deficient subjects.

Broadly, the present invention is based on a study described in the examples that showed that while levels of hepatic iron were increased in mice treated with the iron supplement ferrous sulphate, treatment with the carboxylate modified ferric hydroxide IHAT did not produce the same effect. This in turn means that carboxylate modified ferric oxo-hydroxides, such as IHAT, are particularly suited to the treatment or prophylaxis of iron deficiency associated with NAFLD or NASH as it avoids undesirable hepatic loading of iron observed with other types of iron supplementation. This means that the present invention can be used in the treatment or prophylaxis of iron deficiency associated with NAFLD or NASH. It also means that subjects may be treated without medical practitioners needing to carefully balance the desire to treat the iron deficiency, while minimising the risks associated with hepatic loading of iron.

Accordingly, in a first aspect, the present invention provides a carboxylate ligand modified ferric iron oxo-hydroxide composition for use in the treatment or prevention of iron deficiency associated with non-alcoholic fatty liver disease (NAFLD) or non-alcoholic steatohepatitis (NASH) in a subject, wherein the carboxylate ligand modified ferric iron oxo-hydroxide has a three dimensional polymeric structure in which the carboxylate ligands are non-stoichiometrically substituted for the oxo or hydroxy groups of the ferric iron oxo-hydroxide so that some of the ligand integrates into the solid phase by formal metal-ligand bonding and/or wherein the three dimensional polymeric structure of the carboxylate ligand modified ferric iron oxo-hydroxide is such that the substitution of the oxo or hydroxy groups by the carboxylate ligands is substantially random.

In a further aspect, the present invention provides the use of a carboxylate ligand modified ferric iron oxo-hydroxide composition in the preparation of a medicament for the treatment or prevention of iron deficiency associated with non-alcoholic fatty liver disease (NAFLD) or non-alcoholic steatohepatitis (NASH) in a subject, wherein the carboxylate ligand modified ferric iron oxo-hydroxide has a three dimensional polymeric structure in which the carboxylate ligands are non-stoichiometrically substituted for the oxo or hydroxy groups of the ferric iron oxo-hydroxide so that some of the ligand integrates into the solid phase by formal metal-ligand bonding and wherein the three dimensional polymeric structure of the carboxylate ligand modified ferric iron oxo-hydroxide is such that the substitution of the oxo or hydroxy groups by the carboxylate ligands is substantially random.

In a further aspect, the present invention provides a method of treating or preventing, including slowing the rate of development of, iron deficiency associated with non-alcoholic fatty liver disease (NAFLD) or non-alcoholic steatohepatitis (NASH), the method comprising administering to a subject in need of treatment a therapeutically effective amount of a carboxylate ligand modified ferric iron oxo-hydroxide composition for use in the treatment or prevention of, wherein the carboxylate ligand modified ferric iron oxo-hydroxide has a three dimensional polymeric structure in which the carboxylate ligands are non-stoichiometrically substituted for the oxo or hydroxy groups of the ferric iron oxo-hydroxide so that some of the ligand integrates into the solid phase by formal metal-ligand bonding and wherein the three dimensional polymeric structure of the carboxylate ligand modified ferric iron oxo-hydroxide is such that the substitution of the oxo or hydroxy groups by the carboxylate ligands is substantially random.

In a further aspect, the present invention provides Iron Hydroxide Adipate Tartrate (IHAT) for use in the treatment or prevention of iron deficiency associated with non-alcoholic fatty liver disease (NAFLD) or non-alcoholic steatohepatitis (NASH) in a subject.

In a further aspect, the present invention provides the use of Iron Hydroxide Adipate Tartrate (IHAT) in the preparation of a medicament for the treatment or prevention of iron deficiency associated with non-alcoholic fatty liver disease (NAFLD) or non-alcoholic steatohepatitis (NASH) in a subject.

In a further aspect, the present invention provides a method of treating or preventing iron deficiency associated with non-alcoholic fatty liver disease (NAFLD) or non-alcoholic steatohepatitis (NASH), the method comprising administering to a subject in need of treatment a therapeutically effective amount of Iron Hydroxide Adipate Tartrate (IHAT).

In aspects of the present invention set out herein, the iron deficiency may be treated by the administration of an iron supplement tablet, capsule or powder comprising a carboxylate ligand modified ferric iron oxo-hydroxide composition. These materials and compositions are preferably formulated for oral delivery.

Embodiments of the present invention will now be described by way of example and not limitation with reference to the accompanying FIGURE. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 1. Total iron content in liver samples. (A) Total liver iron content in vehicle controls (n=24), IHAT-gavaged animals (n=24) and FeSO$_4$-gavaged animals (n=24). (B) Total liver iron content over time. Tissues were harvested after 28 days (white bars) and 90 days (grew bars) of oral administration. N=12 animals in each group.

DETAILED DESCRIPTION

Production of Carboxylate Ligand Modified Ferric Iron Hydroxides

The carboxylate ligand modified ferric iron oxo-hydroxides used in accordance with the present invention may be produced using the methods disclosed in WO 2008/096130 or WO 2017/060441, the content of which are expressly incorporated by reference in the entirety. The materials may be produced under specific conditions by dissolving a suitable ferric iron [Fe(III)] salt and then inducing the formation of polymeric iron oxo-hydroxides in which a proportion of the carboxylate ligands become integrated into the solid phase through formal metal-iron (M-L) bonding, i.e. not all of the ligand (L) is simply trapped or adsorbed in the bulk material. The bonding of the metal ion in the materials can be determined using physical analytical techniques such as X-ray diffraction (XRD) or Fourier-transform infrared spectroscopy (FTIR), which demonstrates disruption of mineral phase, i.e. with peak shifts and band broadening due increased amorphousness resulting from ligand incorporation in the primary particle.

In the carboxylate-ligand-modified iron oxo-hydroxides disclosed herein, the presence of formal metal ion-ligand bonding is one feature that distinguishes the materials from other products such as "iron polymaltose" (Maltofer) in which particulate crystalline iron hydroxide is surrounded by a sugar shell formed from maltose and thus is simply a mixture of iron oxo-hydroxide and sugar at the nano-level (Heinrich (1975); Geisser and Müller (1987); Nielsen et al (1994; U.S. Pat. No. 3,076,798); US2006/0205691).

In addition, the carboxylate-ligand modified ferric iron hydroxides of the present invention are solid phase metal poly oxo-hydroxides modified by non-stoichiometric ligand incorporation. This distinguishes them from the numerous metal-ligand classical coordination complexes that are well reported in the art (WO 03/092674, WO 06/037449) which are stoichiometric. Although generally soluble, such complexes can be precipitated from solution at the point of supersaturation, for example ferric trimaltol, Harvey et al. (1998), WO 03/097627; ferric citrate, WO 04/074444, US 2008/0274210 and ferric tartrate, Bobtelsky and Jordan (1947) and, on occasions, may even involve stoichiometric binding of hydroxyl groups (for example, ferric hydroxide saccharide, U.S. Pat. No. 3,821,192).

Without modification, the primary particles of the carboxylate ligand modified ferric iron oxo-hydroxides used herein have ferric iron oxide cores and ferric hydroxide surfaces and within different disciplines may be referred to as metal oxides or metal hydroxides. The use of the term "oxo-hydroxy" or "oxo-hydroxide" and "hydroxide" may be used interchangeably and is intended to recognise these facts without any reference to proportions of oxo or hydroxy groups. As described herein, the carboxylate ligand modified ferric iron hydroxides of the present invention are altered at the level of the primary particle of the metal hydroxide with at least some of the ligand being introduced into the structure of the primary particle, i.e. leading to doping or contamination of the primary particle by the ligand. This may be contrasted with the formation of nano-mixtures of metal oxo-hydroxides and an organic molecule, such as iron saccharidic complexes, in which the structure of the core is not so altered.

The primary particles of the carboxylate ligand modified ferric iron hydroxides materials described herein are generally produced by precipitation. The use of the term "precipitation" often refers to the formation of aggregates or agglomerates of materials that do separate from solution by sedimentation or centrifugation. Here, the term "precipitation" is intended to describe the formation of all solid phase material, including agglomerates or other solid phase materials that remain as non-soluble moieties in suspension, whether or not they be particulate, colloidal or sub-colloidal and/or nanoparticulates or yet smaller clusters.

In the present invention, reference may be made to the carboxylate ligand modified ferric iron oxo-hydroxides having three dimensional polymeric structures that generally form above the critical precipitation pH. As used herein, this should not be taken as indicating that the structures of the materials are polymeric in the strict sense of having a regular repeating monomer unit because, as has been stated, ligand incorporation is, except by co-incidence, non-stoichiometric. Without wishing to be bound by any particular theory, the inventors believe that the carboxylate ligand species is introduced into the solid phase structure by substituting for oxo or hydroxy groups of the forming two dimensional iron oxo-hydroxide chains which then cross-link to form three dimensional structures and so the ligand leads to a change in solid phase order. In some cases, for example the production of the ferric iron materials exemplified herein, the ligand species may be introduced into the solid phase structure by the substitution of oxo or hydroxy groups by ligand molecules in a manner that decreases overall order in the solid phase material. While this still produces solid carboxylate ligand modified ferric iron hydroxides that in the gross form have one or more reproducible physicochemical properties, the materials have a more amorphous nature compared, for example, to the structure of the corresponding unmodified metal oxo-hydroxide. The presence of a more disordered or amorphous structure can readily be determined by the skilled person using techniques well known in the art. One exemplary technique is transmission electron microscopy (TEM). High resolution transmission electron microscopy allows the crystalline pattern of the material to be visually assessed. It can indicate the primary particle size and structure (such as d-spacing), give some information on the distribution between amorphous and crystalline material, and show that the material possesses a structure consistent with a 2-line ferrihydrite-like structure even when modified. Using this technique, it is apparent that the chemistry described above increases the amorphous phase of materials described herein compared to corresponding materials without the incorporated ligand. This may be especially apparent using high angle annular dark field aberration-corrected scanning transmission electron microscopy due to the high contrast achieved while maintaining the resolution, thus allowing the surface as well as the bulk of the primary particles of the material to be visualised.

Generally, in the compositions of carboxylate ligand modified ferric iron oxo-hydroxide used in the present invention have a mean primary particle diameters of 1 to 50 nm, more preferably 1 to 20 nm and even more preferably 1 to 10 nm, for example as determined by electron microscopy. Preferably at least 70%, more preferably at least 80% and most preferably at least 90% of the primary particles in any composition have mean particle diameters falling within these ranges. Mean diameters can be calculated on a "number of particles basis" or per "volume of particles", with calculations per volume of particles providing a better link to the metal concentrations in the various fractions (e.g. % of iron in the nanoparticulate fraction).

Additionally or alternatively, upon ligand modification, the kinetics of dissolution of the carboxylate ligand modified ferric iron hydroxides are accelerated, for example as illustrated in the lysosomal assay, compared to the corresponding materials without the incorporated ligand. In a lysosomal assay, ligand-modified iron oxo-hydroxide (0.9 mM±0.15 mM iron) was incubated in 10 mM citric acid+0.9% NaCl at room temperature, maintaining pH in the 4.9-5.1 range for 6 h. Subsequently, the soluble fraction was isolated by ultrafiltration (3 KDa) and determined by inductively coupled plasma optical emission spectrometry (ICP-OES). Examples of the properties that can be usefully modulated for materials used for iron supplementation or fortification include: dissolution (rate and pH dependence), adsorption and absorption characteristics, reactivity-inertness, melting point, temperature resistance, particle size, surface charge, density, light absorbing/reflecting properties, compressibility, colour and encapsulation properties. Examples of properties that are particularly relevant to the field of supplements or fortificants are physicochemical properties selected from one or more of a dissolution profile, an adsorption profile or a reproducible elemental ratio. In this context, a property or characteristic may be reproducible if replicate experiments for ethanolic recovery are reproducible within a standard deviation of preferably ±20%, and more preferably ±10%, and even more preferably within a limit of ±5%.

The dissolution profile of the solid ligand-modified poly oxo-hydroxy metal ion materials can be represented by different stages of the process, namely dispersion or re-suspension. The term dissolution is used to describe the passage of a substance from solid to soluble phase.

In the carboxylate ligand modified iron hydroxides produced by the methods disclosed herein, the carboxylate ligands may be one, two, three or four or more carboxylate ligands in the form of the carboxylate ion or the corresponding carboxylic acid. Generally, the ligand is a dicarboxylic acid ligand, and may be represented by the formula HOOC—$R_1$—COOH (or an ionised form thereof), where $R_1$ is an optionally substituted $C_{1-10}$ alkyl, $C_{1-10}$ alkenyl or $C_{1-10}$ alkynyl group. The use of ligands in which $R_1$ is a $C_{1-10}$ alkyl group, and more preferably is a $C_{2-6}$ alkyl group, is preferred. Preferred optional substituents of the $R_1$ group include one or more hydroxyl groups, for example as present in malic acid. These ligands include carboxylic acids such as adipate/adipic acid, tartrate/tartaric acid, glutarate/glutaric acid, malate/malic acid, succinate/succinic acid, aspartate/aspartic acid, pimelate/pimelic acid, citrate/citric acid, lactate/lactic acid or benzoate/benzoic acid. In the production of some preferred materials, such as IHAT, two different ligands are used, such as adipate/adipic acid and tartrate/tartaric acid. Other examples of preferred combinations of ligands include tartrate/tartaric acid and succinate/succinic acid. Particularly preferred materials are formed using the following molar ratios of ligands and Fe(III):

| Material | Ligands | Molar Ratio ligand:Fe |
| --- | --- | --- |
| Nano Fe(III) (a) "IHAT" | Tartaric acid (T) Adipic acid (A) | 1:1:2 (T:A:Fe) |
| Nano Fe(III) (b) "IHAT" | Tartaric acid (T) Adipic acid (A) | 0.2:1:2 (A:T:Fe) |
| Nano Fe(III) (c) | Tartaric acid (T) Succinic acid (S) | 1:1:2 (T:S:Fe) |
| Nano Fe(III) (d) | Tartaric acid (T) Succinic acid (S) | 1:6:2 (T:S:Fe) |

Without wishing to be bound by any particular theory, the present inventors believe that in the class of materials referred to herein as "IHAT", it is the tartrate/tartaric acid ligands that are mostly responsible for the disruption of the iron hydroxide structure of the primary particles (Nanomedicine, 10(8): 1877-1886, 2014). In view of this observation, in a further embodiment, the carboxylate ligand modified iron hydroxides may be modified by tartrate/tartaric acid as the sole carboxylate ligand.

The ratio of the ferric iron ion(s) to the carboxylate ligands can be varied according to the methods disclosed herein and may vary one or more properties of the materials. Generally, the useful ratios of M:L will be between 10:1, 5:1, 4:1, 3:1, 2:1 and 1:1 and 1:2, 1:3, 1:4, 1:5 or 1:10, and preferably between 4:1 and 1:1. By way of example, in the preferred class of IHAT materials, the concentration of ferric iron ions may be between 20 mM and 80 mM, the concentration of adipate is between 10 mM and 40 mM and the concentration of tartrate is between 10 mM and 40 mM. In the synthesis of IHAT, a concentration of ferric iron of about 40 mM was used with 20 mM adipic acid and 20 mM tartaric acid. Alternatively, and in particular where different ratios of the components are used, the concentration of ferric iron may be between 20 mM and 500 or 1000 mM, the concentration of adipate may be between 10 mM and 150 mM and the concentration of tartrate may be between 10 mM and 250 mM or 500 mM. In some formulations used in accordance with the present invention, the ligand used to modify the ferric oxo-hydroxide is tartrate/tartaric acid alone, i.e. the materials are made without the inclusion of adipate, but otherwise using the ratios and concentration of species set out above.

In the case of materials using tartrate/tartaric acid as the sole carboxylate ligand, or where adipate is capped at its maximum aqueous concentration (e.g. 150 mM at room temperature), a higher concentration of ferric iron ions may be used between a lower limit 80 mM, 100 mM and 120 mM and an upper limit of 250 mM, 350 mM, 500 mM and 1000 mM, optionally in combination with a concentration of tartrate/tartaric acid between 20 mM and 250 mM or 500 mM.

In a further embodiment, IHAT may be produced using a non-aqueous solvent, such as ethanol, to induce the aggregation of the ligand modified ferric iron hydroxide colloids thus aiding the subsequent recovery of the resulting aggregated material through filtration or centrifugation. The method comprising: mixing a colloidal suspension of the carboxylate ligand modified ferric iron hydroxide in a water miscible non-aqueous solvent to cause the carboxylate ligand modified ferric iron hydroxide to agglomerate; recovering the agglomerated carboxylate ligand modified ferric iron hydroxide; and drying the carboxylate ligand modified ferric iron hydroxide to produce the carboxylate ligand modified ferric iron hydroxide formulation.

In a further embodiment, IHAT formulations produced using a non-aqueous solvent may not retain the synthetic molar ratios. In the case of IHAT materials with a starting synthetic molar ratio of 0.2:1:2 (A:T:Fe) and that are recovered using ethanol, the molar ratios in the recovered formulation may range between 0.03:2 and 0.12:2 for adipate:iron and may range between 0.5:2 and 1:2 for tartrate to iron.

The present invention may employ any way of forming hydroxide ions at concentrations that can provide for hydroxy surface groups and oxo bridging in the formation of the carboxylate ligand modified ferric iron hydroxide materials. Examples include but are not limited to, alkali solutions such as sodium hydroxide, potassium hydroxide and sodium bicarbonate.

Formulations and Uses

Non-alcoholic fatty liver disease (NAFLD) is a condition in which excess fat is stored in your liver that is not caused by heavy alcohol use. NAFLD can progress to non-alcoholic steatohepatitis (NASH), cirrhosis and eventually hepatocellular carcinoma. NASH is diagnosed from histopathological examination of a liver biopsy where this shows fat along with inflammation and damage to liver cells. Fat without inflammation or damage is called fatty liver disease, more correctly called non-alcoholic fatty liver disease (NAFLD). NASH likely affects 3-4% in the United States population whilst NAFLD is becoming the most common liver disease worldwide with an estimated prevalence of 25%-30%.

Importantly, while one third of adult patients with NAFLD are considered to be iron deficient, there is evidence that iron is a co-factor in the pathogenesis of NASH. This means that it would be considered undesirable to have hepatic loading of iron in NAFLD (as a risk factor that could convert it to NASH), or in NASH itself (as a co-morbidity issue). As a patient group, subjects with NALFD or NASH represent about a quarter of all iron deficient subjects.

As the experiments shown in the examples demonstrate that the carboxylate ligand modified ferric iron hydroxides do not accumulate in the liver, unlike other forms of iron supplements such as ferrous sulphate, this opens up the possibility of treating NALFD and NASH, prophylactically or therapeutically, without the risks associated with prior art treatments that cause hepatic iron accumulation. This means that the therapies according to the present invention do not require testing for iron deficiency in NAFLD or NASH patients before treatment with the iron supplements of the present invention. It also allows the iron supplements of the present invention to be administered prophylactically to NAFLD or NASH patients as a precaution against a risk of developing iron deficiency.

The carboxylate ligand modified ferric iron hydroxides produced by the methods of the present invention may be formulated for use as supplements, and especially as therapeutic iron supplements. This means that the formulations may be mixed with one or more pharmaceutically acceptable excipients, carriers, buffers, stabilisers or other materials well known to those skilled in the art. Such materials should be non-toxic and should not interfere with the efficacy of the carboxylate ligand modified ferric iron hydroxides for iron supplementation.

The precise nature of the carrier or other component may be related to the manner or route of administration of the composition, in the present case generally via gastrointestinal delivery, in particular oral delivery. Pharmaceutical compositions for oral administration may be in tablet, capsule, powder, gel or liquid form. In some instances, the materials may be directly orally taken, while in other embodiments, they may be provided in a form suitable for mixing with food or drink and taken in this manner. The latter may be termed fortification but the terms supplement and supplementation are herein included to cover this as well as usual supplement practice.

Tablets are formed by compressing an active substance with components to enable the formation of the tablet and its dissolution after it has been taken by a subject. Accordingly, a tablet may include a solid carrier, such as gelatin or an adjuvant or carrier, a compressibility agent and/or a flowing agent. In the present invention, an iron supplement in the form of a tablet may comprise one or more of the carboxylate ligand modified ferric iron hydroxides (for example forming 5-60% (w/w) of the tablet) and one or more fillers, disintegrants, lubricants, glidants and binders (for example forming the remaining 40-95% (w/w) of the tablet). In addition, the tablet may optionally comprise one or more coatings, for example to modify dissolution of the tablet for either quick or sustained release, and/or one or more coatings to disguise the taste of the tablet or to make it easier for a subject to take orally.

Generally, capsules are formed by enveloping an active substance in a gelatinous envelope. As with tablets, capsules may be designed for quick or sustained release depending on the properties of the envelope or a coating provided on it. Release of the active substance may also be controlled by modifying the particle size(s) of the active substance contained with the envelope. Capsules are generally either hard shelled or soft shelled. Hard shelled capsules are typically made using gelatin to encapsulate the active substance and may be formed by processes such as extrusion or spheronisation. Hard shelled capsules may be formed by sealing together two half shells to form the final capsule. Soft shelled capsules are generally formed by suspending an active ingredient in oil or water and then forming the envelope around the drops of the liquid. Other components of capsules include gelling agents, plant polysaccharides, plasticizers, e.g. for modulating the hardness of the capsule, colouring agents, preservatives, disintegrants, lubricants and coatings.

The carboxylate ligand modified ferric iron hydroxides used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

By way of example, iron supplements are generally administered at doses of between 100 mg Fe to 250 mg Fe per day, and often at doses between 50 mg Fe and 80 mg Fe (e.g. about 60 mg Fe) three times a day (t.d.s.). Other doses that can be used in accordance with the present invention include doses of between about 10 mg Fe and about 50 mg Fe, more preferably between about 15 mg Fe and about 40 mg Fe and most preferably between about 18 mg Fe and about 35 mg Fe. Single dosing may be possible using a sustained release formulation. Prophylactic supplementation may use lower doses, but it is desirable to have any dose containing as high a percentage of the active agent (iron) as possible as this will minimise the size of the dose (capsule, pill etc.). In this aspect, this invention minimises non-active ingredients, such as unreacted ligands, of the formulation and allows the active iron material to be well concentrated in the oral delivery dose.

The carboxylate ligand modified ferric iron hydroxides may be used as supplements for nutritional or medical benefit. In this area, there are three main examples:
 (i) Therapeutic (prescription) supplements, which are generally administered orally for the treatment of indications including iron deficiency anaemia, iron deficiency and anaemia of chronic disease. The therapeutic administration of carboxylate ligand modified ferric iron hydroxides of the present invention may be in conjunction with other therapies, for example with the concomitant use of erythropoietin.
 (ii) Nutritional supplements (self prescribed/purchased supplements) which are usually for oral delivery.
 (iii) Fortificants. These may be traditional forms—in terms of being added to food prior to purchase—or more recent fortificant forms such as 'Sprinkles' which are added (like salt or pepper) to food at the time of ingestion.

In all formats, but most especially for fortificants, subsequent formulation, such as addition of a protective coating (e.g. lipid), may be necessary to make the material compatible with its intended usage. In addition, any of these supplemental forms can be co-formulated, either by incorporation within the material through use of co-formulated material(s) as ligand(s) or through trapping/encapsulation of said materials, or simply through co-delivery of said materials.

EXAMPLES

Materials and Methods

Iron Materials

Two iron materials were tested in this study: i) Iron Hydroxide Adipate Tartrate (IHAT), as manufactured by Huvepharma, Italy, and ii) ferrous sulphate ($FeSO_4$). IHAT was suspended in purified water (ROTIPURAN® p.a., ACS) at a concentration of 51.1 mM iron (11.55 mg IHAT/mL), and $FeSO_4$ at a concentration of 35.81 mM iron (5.93 mg $FeSO_4$/mL). These suspensions were prepared freshly on the day of administration and used for gavage in the animal study as outlined below within a time period of 5 hours post preparation.

Animal Study

This study was approved by the institutional animal ethics committee (VivoScience GmbH, Germany) and was in accordance with Directive 2010/63/EU and Directive CETS No. 123. Every effort was made to minimise suffering.

5-6 week old Wistar rats (n=72; 36 female and 36 male) were housed in harmonious social groups (2-3 animals per cage and sex) in a light- and temperature-controlled room with ad libitum access to standard pellet diet and water. Rats were acclimatised for 7 days for male rats and 14 days for female rats, prior to treatment commencement.

Rats were randomly assigned to one of three groups: i) IHAT (n=24, 12 female and 12 male), ii) $FeSO_4$ (n=24, 12 female and 12 male) or iii) vehicle control group (ROTIPURAN® p.a., ACS, n=24, 12 female and 12 male). The Iron materials (IHAT: 51.1 mM iron; $FeSO_4$: 35.81 mM iron) and the control water were daily administered to animals by oral gavage at 10 mL/kg body weight. Resulting iron concentrations were as follows: IHAT group: 28.5 mg iron/kg body weight; $FeSO_4$ group: 20.00 mg iron/kg body weight. Animals were gavaged for 28 days (n=36; 18 female and 18 male) or 90 days (n=36; 18 female and 18 male). Following necropsy, livers were harvested, flash frozen in liquid nitrogen and stored at −80° C. until further analysis.

Liver Total Iron Content

Livers were thawed at room temperature, and a sample of approximately 800 mg was cut out, cleaned from any fat and weighed on a balance accurate to 0.0001 g. Weighed samples were digested in concentrated $HNO_3$ (Nitric acid ≥65%, 84380-2.5L-M, Merck) and $H_2O_2$ (Hydrogen peroxide solution, 16911-1L-F, Sigma-Aldrich) at a 5:1 ratio. Samples were digested at room temperature for 24 h and if necessary at 40° C. for another 24 h to allow complete digestion. Following complete digestion samples were diluted 1:4 in UHP water to achieve a final $HNO_3$ concentration of 6-8%. Total elemental analysis for iron was carried out on a Jobin Yvon Horiba Ultima 2C ICP-OES (Instrument SA, Longjumeau, France), equipped with a concentric nebulizer and cyclonic spray chamber. Analysis was by peak profile with a window size of 0.025 nm with 21 increments per profile and an integration time of 0.5 seconds per increment. Analytical line was 259.940 nm. Samples and blanks were analysed with iron standards (0-20 mg/L) prepared in 6-8% HNO3, using a 1000 mg/L Fe ICP solution. Pooled-sample standards (0-20 mg/L) were prepared, using a pool of all final digests, to allow detection of possible matrix effects. Each sample/blank/standard was analysed in triplicates and the average value used for the calculations. The sample induction system (sample tubing, nebuliser and spray chamber) was thoroughly flushed between samples, blanks and standards.

Statistical Analysis

Statistical analyses were performed in GraphPad Prism 6. One-way ANOVA, followed by Tukey's multiple comparison's test, was used to assess the treatment effect, irrespective of the length of treatment. Two-way ANOVA was used to assess the effects of time (i.e. treatment length), treatment and the time x treatment interactions, followed by Bonferroni's multiple comparisons test. Two-way ANOVA was also used to assess the effect of sex, treatment and the sex x treatment interaction. P values <0.05 were considered significant in all analyses. Data are presented as means±SDs.

Results

FIG. 1 shows the total iron content in liver samples. Whilst the iron concentrations are similar in the IHAT and the control group, there is a significant difference between the $FeSO_4$ and the control group: Total iron contents in liver samples of $FeSO_4$-gavaged animals are significantly increased in relation to vehicle-gavaged animals (FIG. 1A). In the $FeSO_4$ group, but not in the IHAT or the control groups, iron seems to accumulate over time (FIG. 1B). Remarkably, female animals show higher iron levels in their livers than male animals for all three groups (FIG. 1C).

TABLE 1

Lysosomal dissolution of 5 independent batches of IHAT with a ratio of 0.2:2:1:2 (tartrate:adipate:Fe)

| Lot | [Fe], mmol/L | % dissolution |
|---|---|---|
| 180001 | 0.84 | 49.7 |
| 180002 | 0.88 | 50.4 |
| 180003 | 1.01 | 57.5 |
| 180004 | 0.87 | 57.3 |
| 180005 | 1.06 | 52.1 |

CONCLUSION

Whilst the data show no difference in total iron contents between the IHAT and the control group, there is, at least for the liver, a significant difference between the $FeSO_4$ and the control group, with levels being higher in the $FeSO_4$ group over time (i.e. accumulation). Collectively, these results indicate (i) IHAT and iron from IHAT do not accumulate with repeated oral dosing, whereas (ii) Iron from $FeSO_4$ does accumulate in a tissue-dependent manner with repeated oral dosing.

REFERENCES

The following references are expressly incorporated by reference for all purposes in their entirety.

Pereira et al., Nanomedicine, 10(8): 1877-1886, 2014. doi: 10.1016/j.nano.2014.06.012

Aslam et al., Ferroportin mediates the intestinal absorption of iron from a nanoparticulate ferritin core mimetic in mice. FASEB J. 28(8):3671-3678, 2014.

Powell et al., A nano-disperse ferritin-core mimetic that efficiently corrects anaemia without luminal iron redox activity. Nanomedicine, 10(7):1529-1538, 2014.

WO 2008/096130.

http://www.rsc.org/chemistryworld/2014/12/solving-iron-solubility-problem-profile-mrc Heinrich. Bioavailability of trivalent iron in oral preparations. Arzeinmittelforshung/Drug Research 1975; 25(3): 420-426.

Geisser & Müller, Pharmacokinetics of iron salts and ferric hydroxide-carbohydrate complexes. Arzneimittelforshung/Drug Research, 37 (1): 100-104, 1987.

Nielsen et al., Bioavailability of iron from oral ferric polymaltose in humans. Arzneimittelforshung/Drug Research, 44(1): 743-748, 1994.

U.S. Pat. No. 3,076,798.

US 2006/0205691.

WO 2003/092674.

WO 2006/037449.

Harvey et al., Ferric trimaltol corrects iron deficiency anaemia in patients intolerant to iron. Alimentary Pharmacology & Therapeutics, 12(9):845-848, 1998.

WO 2003/097627.

Bobtelsky M and Jordan J. The structure and behaviour of ferric tartrate and citrate complexes in dilute solutions. J.A.C.S., 69: 2286-2290, 1947.

U.S. Pat. No. 3,821,192.

The invention claimed is:

1. A method for the treatment or prevention of iron deficiency associated with non-alcoholic fatty liver disease (NAFLD) or non-alcoholic steatohepatitis (NASH) in a subject in need thereof, comprising administering a carboxylate ligand modified ferric iron oxo-hydroxide composition to the subject,
wherein the carboxylate ligand modified ferric iron oxo-hydroxide has a three dimensional polymeric structure in which the carboxylate ligands are non-stoichiometrically substituted for the oxo or hydroxy groups of the ferric iron oxo-hydroxide so that some of the ligand integrates into the solid phase by formal metal-ligand bonding, and/or
wherein the three dimensional polymeric structure of the carboxylate ligand modified ferric iron oxo-hydroxide is such that the substitution of the oxo or hydroxy groups by the carboxylate ligands is substantially random.

2. The method of claim 1, wherein the subject has iron deficiency associated with non-alcoholic fatty liver disease (NAFLD).

3. The method of claim 1, wherein the subject has iron deficiency associated non-alcoholic steatohepatitis (NASH).

4. The method of treatment of claim 1, wherein the method is for the prophylactic treatment of a subject with non-alcoholic fatty liver disease (NAFLD) or non-alcoholic steatohepatitis (NASH) who is at risk of developing iron deficiency.

5. The method of claim 1, wherein the method is for therapeutic treatment of a subject with iron deficiency associated with non-alcoholic fatty liver disease (NAFLD) or non-alcoholic steatohepatitis (NASH).

6. The method of claim 1, wherein the method further comprises testing the subject with non-alcoholic fatty liver disease (NAFLD) or non-alcoholic steatohepatitis (NASH) to determine whether the subject has iron deficiency.

7. The method of claim 1, wherein the ligands used to modify the ferric iron oxo-hydroxide comprise one or more of adipate/adipic acid, tartrate/tartaric acid, glutarate/glutaric acid, malate/malic acid, succinate/succinic acid, aspartate/aspartic acid, pimelate/pimelic acid, citrate/citric acid, lactate/lactic acid, or benzoate/benzoic acid.

8. The method of claim 7, wherein the ligands used to modify the ferric iron oxo-hydroxide are selected from one or more of adipate/adipic acid, tartrate/tartaric acid, and succinate/succinic acid.

9. The method of claim 8, wherein the ligands used to modify the ferric iron oxo-hydroxide are tartaric acid and adipic acid.

10. The method of claim 7, wherein the ligands used to modify the ferric iron oxo-hydroxide comprise adipate and tartrate ligands, or tartrate and succinate ligands, or succinate and adipate ligands.

11. The method of claim 7, wherein the ligands used to modify the ferric iron oxo-hydroxide ferric iron oxo-hydroxide formulation comprise tartrate ligands.

12. The method of claim 11, wherein the ligands used to modify the ferric iron oxo-hydroxide ferric iron oxo-hydroxide formulation comprise tartrate ligands in combination with a further ligand.

13. The method of claim 12, wherein the ligands used to modify the ferric iron oxo-hydroxide ferric iron oxo-hydroxide formulation comprise tartrate ligands in combination with adipate ligands.

14. The method of claim 13, wherein the ligands used to modify the ferric iron oxo-hydroxide consist of tartrate ligands in combination with adipate ligands.

15. The method of claim 8, wherein the ligands and ferric iron ions are present in a molar ratio of 1:1:2 or 0.2:1:2 (adipate: tartrate:Fe), 1:1:2 (tartrate: succinate: Fe), 1:6:2 (tartrate: succinate), 1:2 (tartrate: Fe) or 1:1:2 (succinate: adipate: Fe).

16. The method of claim 1, wherein the carboxylate ligand modified ferric iron oxo-hydroxide is Iron Oxo-hydroxide Adipate Tartrate (IHAT).

17. The method of claim 1, wherein the carboxylate ligand modified ferric iron oxo-hydroxides have a mean primary particle diameter size between 1 to 10 nm as determined by electron microscopy.

18. The method of claim 1, wherein the ligand interaction with the iron oxo-hydroxide is detectable by a physical analytical technique as determined by Fourier-transform infrared spectroscopy (FTIR) or X-ray diffraction (XRD).

19. The method of claim 1, wherein the carboxylate ligand modified ferric iron oxo-hydroxide has a greater lability for releasing iron into a solution phase than the corresponding unmodified iron oxo-hydroxide.

20. The method of claim 19, wherein the lability of the carboxylate ligand modified ferric iron oxo-hydroxide is measured using a lysosomal assay, wherein at a 0.9 mM (±0.15 mM) iron, the release of iron into the solution phase from the modified iron oxo-hydroxide is greater than from the unmodified iron oxo-hydroxide.

21. The method of claim 1, wherein the carboxylate ligand modified ferric iron oxo-hydroxide is produced through a method comprising:
mixing a colloidal suspension of the carboxylate ligand modified ferric iron hydroxide in a water miscible non-aqueous solvent to cause the carboxylate ligand modified ferric iron hydroxide to agglomerate;
recovering the agglomerated carboxylate ligand modified ferric iron hydroxide; and
drying the carboxylate ligand modified ferric iron hydroxide to produce the carboxylate ligand modified ferric iron hydroxide formulation.

22. The method of claim 21, wherein the molar ratio of iron, adipate and tartrate in the recovered formulation are between 0.03:2 and 0.12:2 for adipate: iron and between 0.5:2 and 1:2 for tartrate: iron.

23. A method for the treatment or prevention of iron deficiency associated with non-alcoholic fatty liver disease (NAFLD) or non-alcoholic steatohepatitis (NASH) in a subject, comprising administering an effective amount of Iron Oxo-hydroxide Adipate Tartrate (IHAT) to the subject.

* * * * *

UNITED STATES PATENT AND TRADEMARK OFFICE
CERTIFICATE OF CORRECTION

| | | |
|---|---|---|
| PATENT NO. | : 12,329,736 B2 | Page 1 of 1 |
| APPLICATION NO. | : 17/915192 | |
| DATED | : June 17, 2025 | |
| INVENTOR(S) | : Massari et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 528 days.

Signed and Sealed this
Sixteenth Day of December, 2025

John A. Squires
*Director of the United States Patent and Trademark Office*